(12) United States Patent
Chien

(10) Patent No.: US 7,455,444 B2
(45) Date of Patent: Nov. 25, 2008

(54) MULTIPLE LIGHT SOURCE NIGHT LIGHT

(76) Inventor: Tseng-Lu Chien, 8F, No. 29, Alley 73, Lin-Shen Road, Shi-Chi Town, Taipei Hseng (TW)

( * ) Notice: Subject to any disclaimer, the term of this patent is extended or adjusted under 35 U.S.C. 154(b) by 62 days.

(21) Appl. No.: 11/255,981

(22) Filed: Oct. 24, 2005

(65) Prior Publication Data

US 2006/0152946 A1 Jul. 13, 2006

Related U.S. Application Data

(63) Continuation-in-part of application No. 11/094,215, filed on Mar. 31, 2005, now abandoned, and a continuation-in-part of application No. 11/092,741, filed on Mar. 30, 2005, now Pat. No. 7,232,251, and a continuation-in-part of application No. 10/883,747, filed on Jul. 6, 2004, now abandoned.

(51) Int. Cl.
*H01R 33/00* (2006.01)
*F21V 23/00* (2006.01)

(52) U.S. Cl. ........................ 362/643; 362/641; 362/642; 362/644

(58) Field of Classification Search .......... 362/641–644
See application file for complete search history.

(56) References Cited

U.S. PATENT DOCUMENTS 5,829,862 A * 11/1998 Ferrell ........................ 362/554
6,431,719 B1 * 8/2002 Lau et al. ..................... 362/95
6,926,426 B2 * 8/2005 Currie et al. ................ 362/282

* cited by examiner

*Primary Examiner*—Sandra O'Shea
*Assistant Examiner*—James W Cranson
(74) *Attorney, Agent, or Firm*—Bacon & Thomas, PLLC

(57) ABSTRACT

A multiple light source night light incorporates at least two sets of light sources to offer perfect illumination for decorative lighting and also for providing area illumination via openings, windows, holes, cut-outs, and/or light-transmitting areas of the housing. The multiple light source sets may include LED or EL elements (including sheet, wire, or tube type elements), neon bulbs or tubes, or the like. In addition, the night light may incorporate an air freshener, fan, mechanical device, O3 generator, potpourri, deodorizer elements, fragrance elements, oil, chemical compounds, sensors, heat elements, and/or switch devices to provide additional functions when the prongs are connected with a power source.

6 Claims, 6 Drawing Sheets

MULTIPLE LIGHT SOURCE NIGHT LIGHT

This application is continuation-in-part of U.S. patent application Ser. Nos. 10/883,747, filed Jul. 6, 2004, now abandoned; 11/092,741, filed Mar. 30, 2005, now U.S. Pat. No. 7,232,251; and Ser. No. 11/094,215, filed Mar. 31, 2005, now abandoned.

BACKGROUND

The Inventor's U.S. Pat. Nos. 5,926,440, 6,158,868, 6,170,958, 6,171,117, 6,280,053 disclose arrangements of conductive means for a night light and multiple function night light incorporated with a time piece. The Inventor's other U.S. Pat. Nos. 4,947,291, 5,495,402, 5,662,408, 5,713,655, 5,803,579, 5,816,682, 5,833,350, 5,893,626, 5,998,928, 6,000,807, 6,010,228, 6,031,958, 6,033,087, 6,056,420, 6,132,072, 6,160,948, 6,161,910, 6,183,101, 6,190,017, 6,290,368, 6,337,946, 6,386,730, 6,390,647, 6,00,104, 6,411,524, 6,431,719, 6,509,832, 6,523,976, 6,550,949, 6,609,812, 6,623,416, 6,641,289, 6,648,496, and 6,709,126 all show different light sources and applications but none teaches a night light incorporated with two light sources for an accent light and a floor light, the night light having different light beam directions to provide illumination for the housing and the floor.

In particular, all existing fiber optic night lights have the major problem of too low light intensity, which only offers an accent or decorative light effect but cannot offer enough light intensity to enable persons to carry out activities in dark areas. The current invention has two sets of light sources, one for accent light and the other for floor illumination, so as to overcome this fatal problem.

The current invention uses multiple light source sets to make a big improvement in the fiber optics night light, by addressing the problem that conventional fiber optic night lights only have decorative light intensity and have lost the major night light function of allowing people to see an area clearly. It also overcome the major problem that LED lights have too narrow viewing angles and therefore cannot broadly illuminate the floor.

The current invention also incorporates a decorative unit to enable the night light to have more fashion designs.

The current invention also may incorporate a smell device to enable the night light to not only offer illumination but also greatly improve ambient smells to let the consumer have peace of mind at any time by fragrance oil, gel, wax with fan, mechanical device, heat elements, and/or a heater film with adjustable functions to make the good smell spread to a wider area.

DRAWINGS

FIG. 1 is a perspective view of a multiple light source night constructed in accordance with a first preferred embodiment of the invention.

FIG. 2 includes a cross-sectional side view of the night light of the first preferred embodiment.

Figure 5:
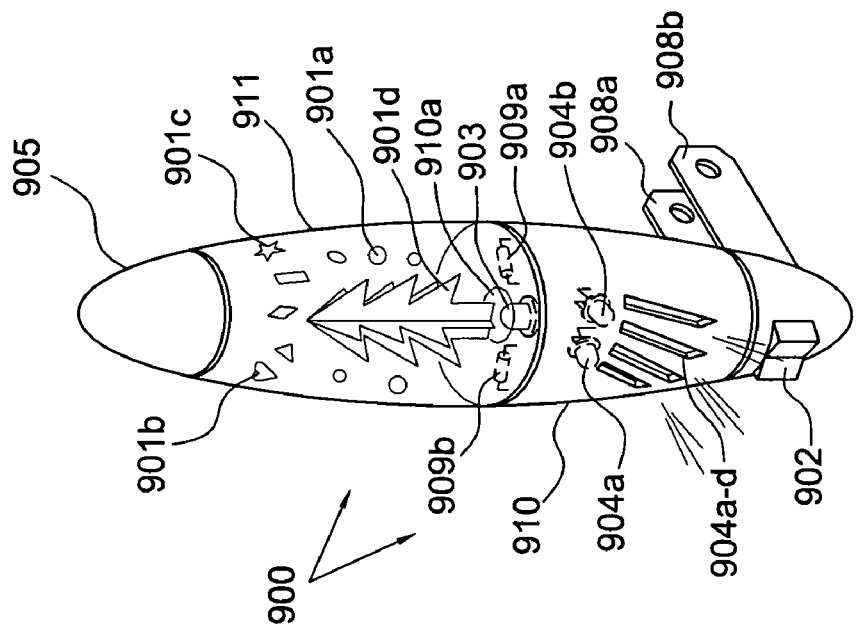

FIG. 5 is a perspective view of a preferred embodiment which has multiple light sources sets for the decorative unit and housing's windows, holes, cut-outs, and/or openings for pre-determined light effects, and a built-in heat element(s) to cause fluid movement in a liquid medium decorative unit and thereby cause movement of inner reflective materials, floating stuffs, and/or poly miniatures for eye-catching effects.

Figure 6:
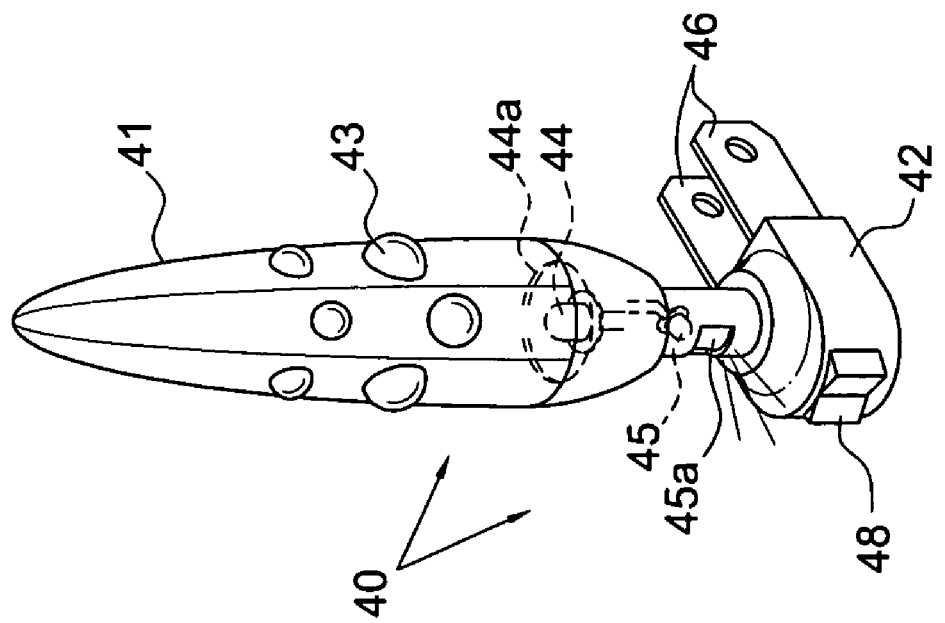

FIG. 6 is a perspective view of a multiple light source set night light in which a first set offers desired light effects to top a solid plastic injection cone with air bubbles inside and the second set provides the light to the housing openings, windows, holes, and/or cut-outs.

Figure 7:
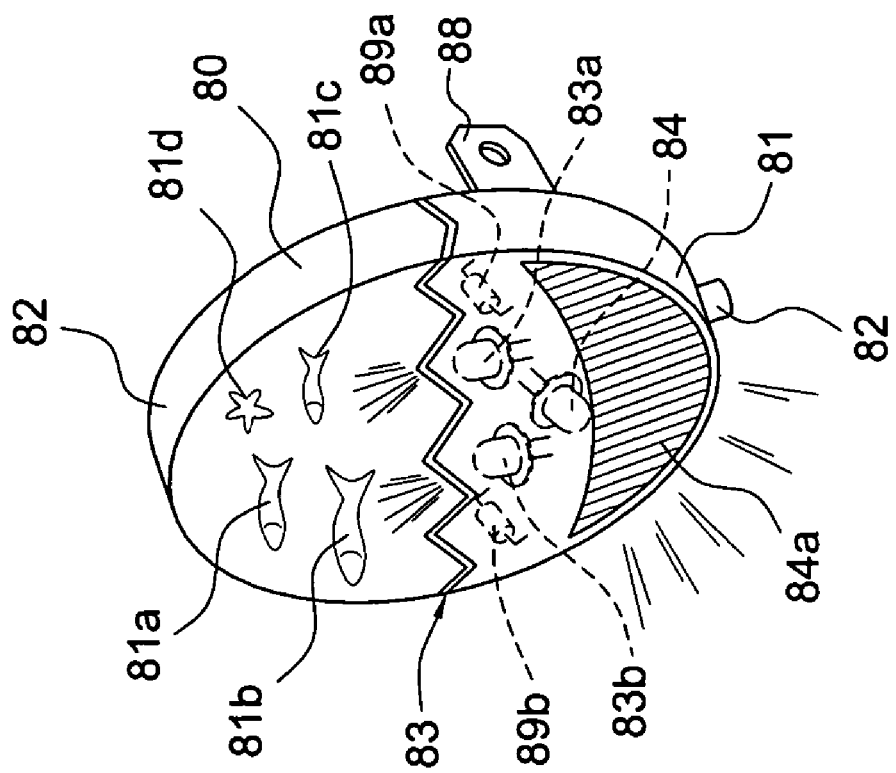

FIG. 7 of a night light with multiple light source sets that provides the desired light effects through a liquid medium container having floating stuffs, reflective materials, and/or poly characters inside by a first light source set and that uses a second light source set to provide light effects to housing openings, holes, windows, cut-outs, and/or areas with transparent or translucent material.

Figure 9:
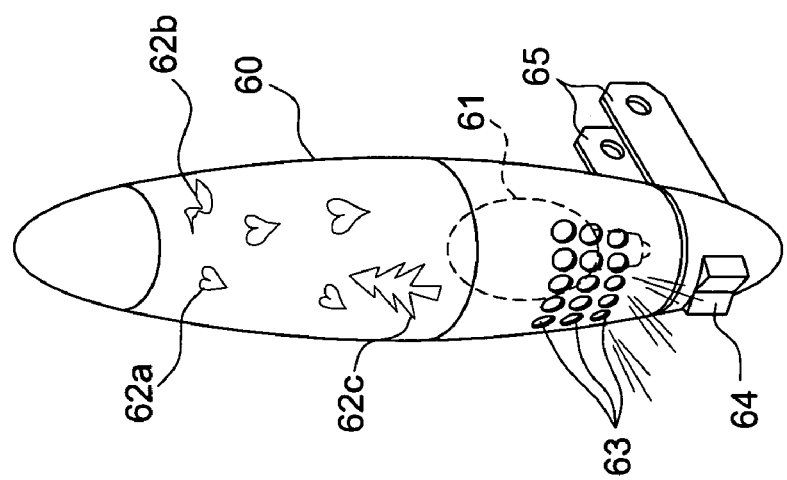
Figure 8:
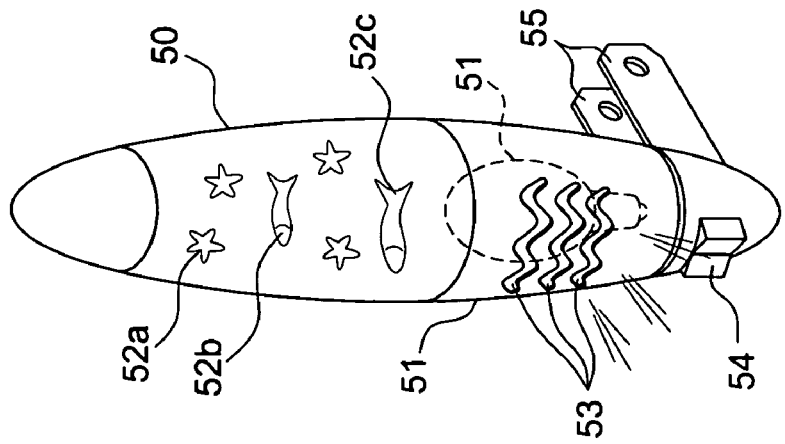

FIG. 8 and FIG. 9 are perspective views of a night light having a single light source for the top decorative unit and a housing including a plurality of windows, openings, cut-outs, and/or holes for illumination, the light source being an incandescent bulb which has a filament inside to produce heat and cause hot air flow upwards in order to cause the top liquid medium container's inside fluid, reflective materials, poly characters, and floating stuffs to have expected functions and get good light effects and cosmetic appearance.

Figure 10:
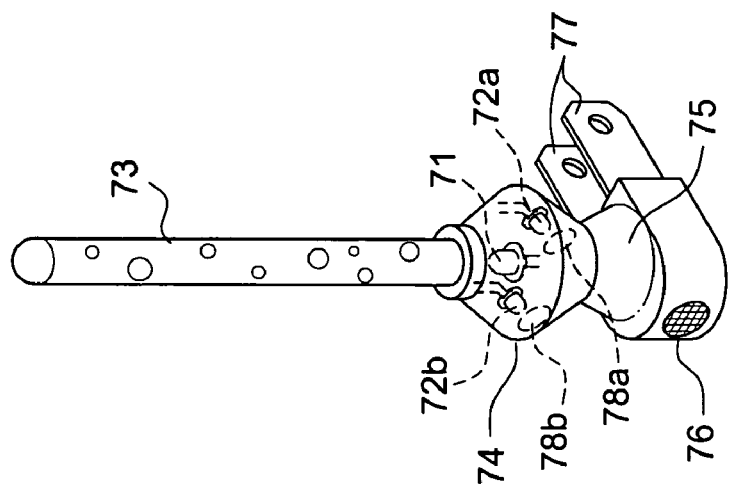

FIG. 10 is a perspective view of a multiple light source night light that use the light passing though material of the housing to eliminate the need for openings, windows, cut-outs, or holes, but which still offers multiple areas through which light is emitted out to viewers.

Figure 11:
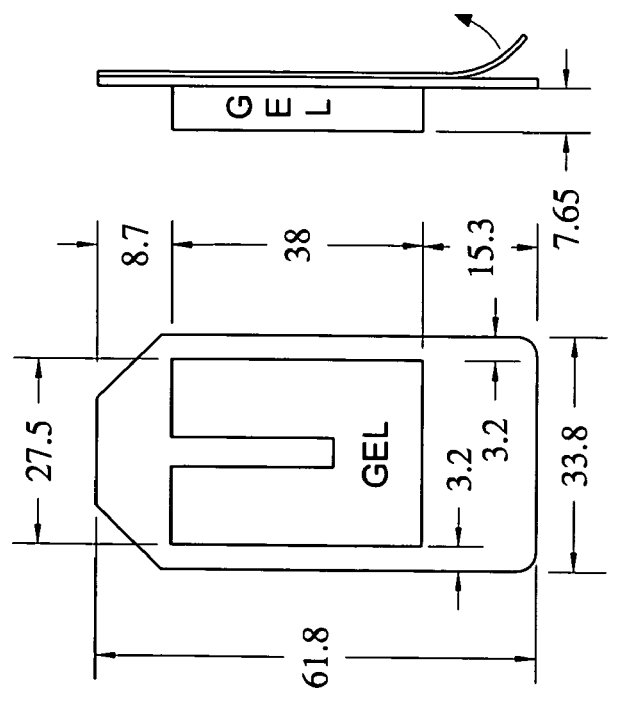

FIG. 11 are front and side views of a preferred fragrance element with a gel within for the night light with smell device.

Figure 12:
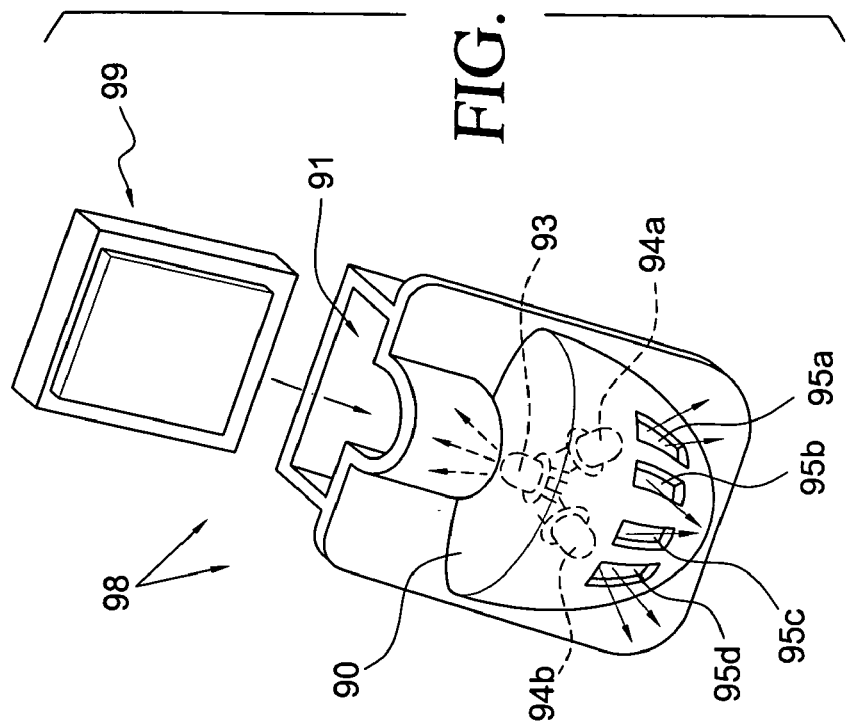

FIG. 12 is a perspective view of an embodiment of the multiple light source night light arranged to accommodate the fragrance element of FIG. 11.

DETAIL DESCRIPTION

Figure 1:
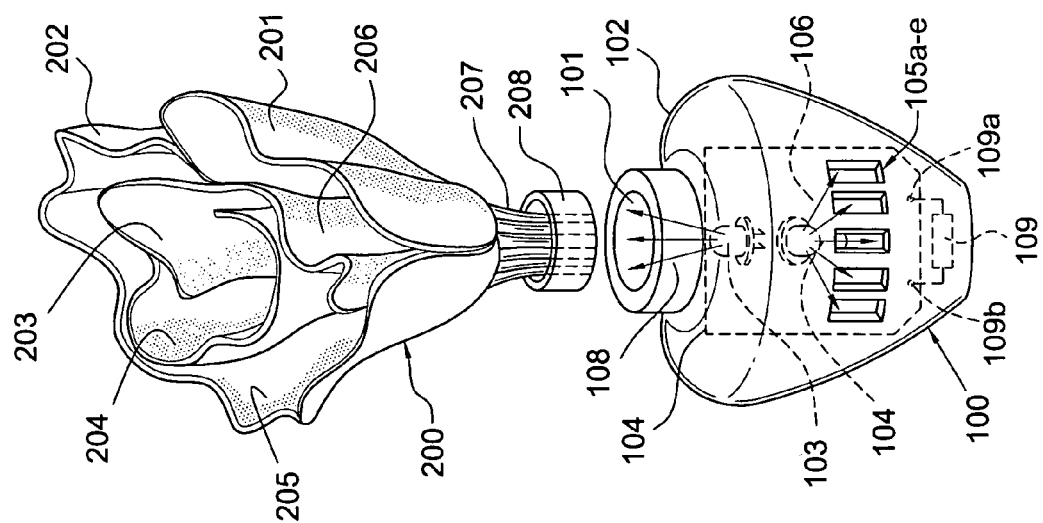

FIG. 1 shows a two light source night light having a fiber optics device (200) on top and a base (100). The base (100) has a circuit (106) inside to allow all electric components and parts to be well installed. At least two light sources (103) and (104) are installed on the circuit board (104). The light sources (103) and (104) may be selected from the group including combinations of an LED, LED(s), EL elements (including sheet, wires, tube type), a neon bulb or bulbs, an incandescent bulb or bulbs, or any other conventional light means available from the marketplace. The preferred first light source (103) is an LED which may take the form of a single sealing piece with a single filament inside or multiple filaments inside to offer a single color or multiple colors from the single sealed LED unit. The preferred first light source (103) also can use multiple pieces of sealed LED(s) instead of a single sealed LED unit. It also can incorporate Red, Green, and Blue sealed LED(s) (R+G+B) with a proper circuit control by an integrated circuit to create automatically changing color light effects. A detailed description of using LEDs with changing color light effects is found in a co-pending filings entitled LED Night Light With Liquid Optical Medium, and Night light with Fiber Optics, both of which teach multiple functions with a manual switch to select the preferred function(s).

The second light source may be in the form of a single filament sealed unit which only offers a single color light output so as to easily let people to see the floor and surrounding items in a dark area. It also can be a multiple filaments sealed unit so as to change the light color to a different one of at least eight available colors provided by an existing market available IC control, and with a manual switch for selecting colors and effects as described in the co-pending applications listed above, or for selecting an automatic color changing mode. Alternative or other functions of the first and second light sources will of course still fall within the scope of the current invention and each light source may be selected from conventional light means or combinations of an LED, LEDs, an EL element, a neon-bulb, a gas-filled bulb, a fluorescent tube for the first or second light source to create the desired light effects. The first or second light source set(s) can each have at least one light means or multiple light means. For example, the 1$^{st}$ light source set may have 1 LED or 3 LED(s). It also can be 3 LED(s) and 2 EL(s).

BecauseLEDs can share the circuit used to change the 110 Volt 60 Hz wall outlet current to an LED trigger voltage and current, the cost of using a multiple piece LED is not substantially more than the cost of using a one piece LED arrangement. Similarly, incorporation of EL elements does not greatly increase the cost since EL elements can be directly driven by the wall outlet current without any circuit needed for low brightness grade illumination. Hence, in a multiple light source set, each set may be any combination of conventional light means from number 1 to number N (N can be any number). This allows the current invention to offer very unique features for applying multiple light source set(s) to the conventional night light and provide a big improvement in low cost light output for decorative units including fiber optics, electroluminescent elements, neon bulbs or the like as discussed above.

FAs shown in FIG. 1, a fiber optics flower (200) is constructed of several pieces of fiber optics textile (201) (202) (203) (204) (205) (206) in certain curvatures and colors to get the shape of a particular flower such as a rose or other flower shape depending on market requirements. Each textile piece has a variety of the fiber optics wires (207) to form at least one bundle having a certain diameter and fastened by a hold means (208). The fiber optics wires may be cut to form a straight end and inserted into the base's opening (101) to form the first light means (103). The base (100) has at least two light source sets (103) and (104). The opening (101) receives the fiber optics bundle and supplies light beams from the light source set (103) to the fiber optics bundle. The other light source (104) provides the light source to the windows' (105a, b,c,d,e) so that each window has a certain light beam (106a, b,c,d,e) pass though in the desired direction to viewer. The second light source set (104) preferably is situated at a certain angle which allows the light beams to pass through the windows in the desired direction. For example, the windows (105a,b,c,d,e) can be located on a lower area of the vise shaped housing (100) and the second light source may have around a 45 degree tilt angle to emit the light to the floor which will create a very good floor illumination. Alternative considerations and different arrangements for the second or more light sources will also fall within the scope of the current invention.

The circuit (106) can supply different electric signals to the first and second light sources so as to meet the first and second light source trigger voltage and current requirements. For example, the EL element can work directly from the wall outlet current for 110V AC 60 Hz, while the LED light source needs to have a proper circuit to convert the outlet current for 110V AC 60 HZ to a voltage and current suitable for causing illumination of an LED or LED(s). When the first and second light sources incorporate integrated circuit (IC chips), the circuit has to offer the right working current to meet each light source trigger specification so that it can turn the light source on under predetermined light effects with certain extra features such as a sensor, manual switch, control means, heater means, or other electric or mechanical means to provide the night light with expected functions and features etc. The first and second light source sets may create different performances for different requirements such as light effects, light brightness, light colors, light emitting directions, light output, light power consumption, light functions, extra functions, light trigger specification, turn on and off time, and other lighting issues. This versatility is made possible by the use of multiple light source sets rather than a single light source, and provides a major advantage of the present invention. Optional parts such as heat element (109) may be installed on the circuit board (106) to offer heat to make the air flow quickly and let the other optional parts such as fragrance gel (500) (same as GLADE refill of Johnson and Johnson), liquid, oil, or wax to spread out quickly to wider areas to provide pleasant smells.

Figure 2:
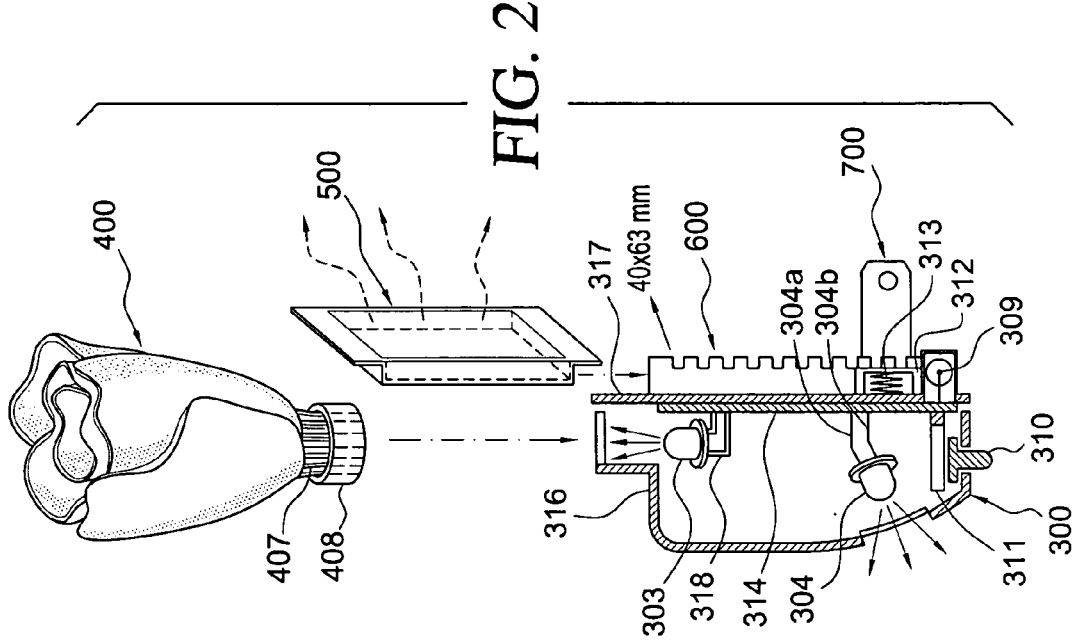

FIG. 2 shows the preferred two light source night light with fragrance dispensing construction. The base (300) has a first light source set (303) and a second light source (304) with a heat element (309) and switch (310) installed on the circuit (314). The circuit (314) is located within the front base (316) and rear base (317). The rear base has an opening to allow a tubular board (312) and inner spring (313) to provide electric delivery from the prong (700) to the circuit (314). This is same principle as disclosed in the Inventor's issued U.S. Pat. Nos. 6,170,958 and 6,171,117 for flexible and conductive plastic or metal material such as resilient spring metal conductive between the prong (700) and circuit board (314) to prevent any gaps and ensure good electrical contact and conduction between the prong and circuit board. Alternative or equivalent means can be applied to ensure conduction, including other conductive means such as conductive wires, conductive and resilient means, springs, a conductive rubber or conductive metal piece such as plate, ribbon etc. Any combination of conductive means or conductive-resilient means will fall within the scope of the invention so long as it ensures electric delivery from one end to other end such as from prong to circuit, or prong to EL panel, or prong to light means. It is noted that use of metal material such as a spring has the advantage of avoiding the need for soldering work, time, labor and missing contact for the prong (700) and circuit board (314). The fragrance gel pack (500) has a fixed dimension and is available in the market place. The preferred compartment (600) has dimensions that can just fit the fragrance gel (500) within to allow easy replacement, for example with outside dimensions of approximately 40 mm (width)×63 mm (length)×1.0 mm (height) and an inner space of around 34 mm (width)×60 mm (length)×7 mm (height). The gel (500) is heated by the heat element (309) so as to cause hot air to flow up and make the gel's smell spread out.

Figure 3:
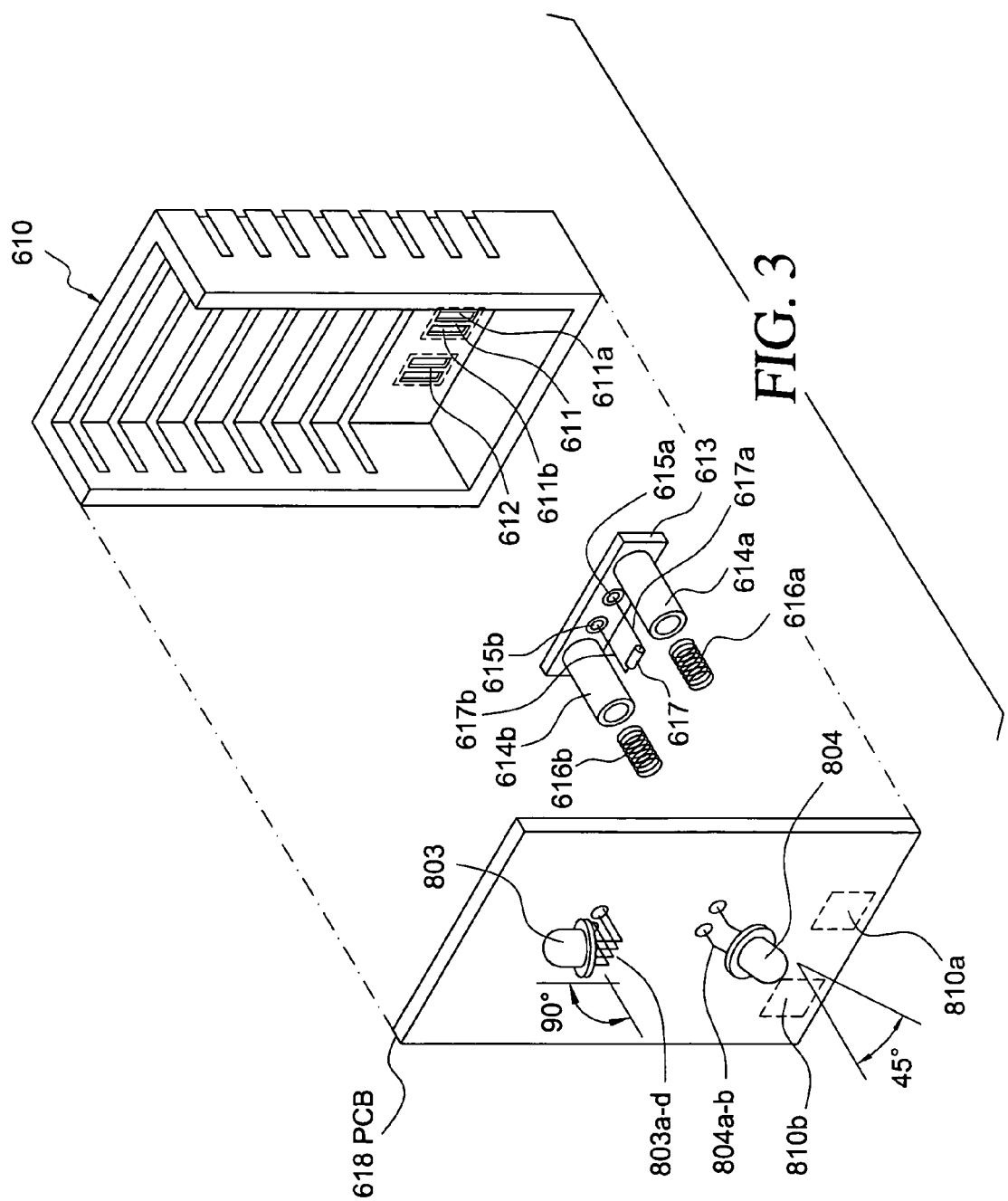
FIG. 3 is an exploded perspective view of a preferred construction to add a fragrance refill to the preferred night light.

FIG. 3 shows details of a fragrance dispenser construction for use in the embodiment of FIG. 2, which may include gel (550) compartment (610) with a lot of open louvers to allow the air flow to pass through. The lower portion includes prong slots (611)(612) to allow the prong means (not shown) to pass through so that the prong's wings (611a) (611b) and (612a) (812b) can fall within insets at predetermined locations. The tubular holder means (613) not only offers two tunnels (614a) (614b) to install the conductive and resilient metal means such as springs (616a) (616b) within the tubular holder means (13) but also hold the prong means wings (611a) (611b) (612a) (612b) tightly and securely so that they will not move under an external force. The conductive means with resilient properties, preferably a metal spring, also delivers an electric signal from the prong means (not shown) to the circuit's contact areas (810a) (810b) so can it can drive the circuit (618) to supply certain electric signals to the two light source sets (803) (804) for desired light effects. An alternative or equivalent arrangement to deliver the electric signals from the prong to the circuit also can use any combination of conductive wire(s), conductive metal pieces, soldering material and process to get the same result to supply electric signals from prong to circuit over a certain distance. These alternative or equivalent arrangements still fall within the scope of the current invention.

Figure 4:
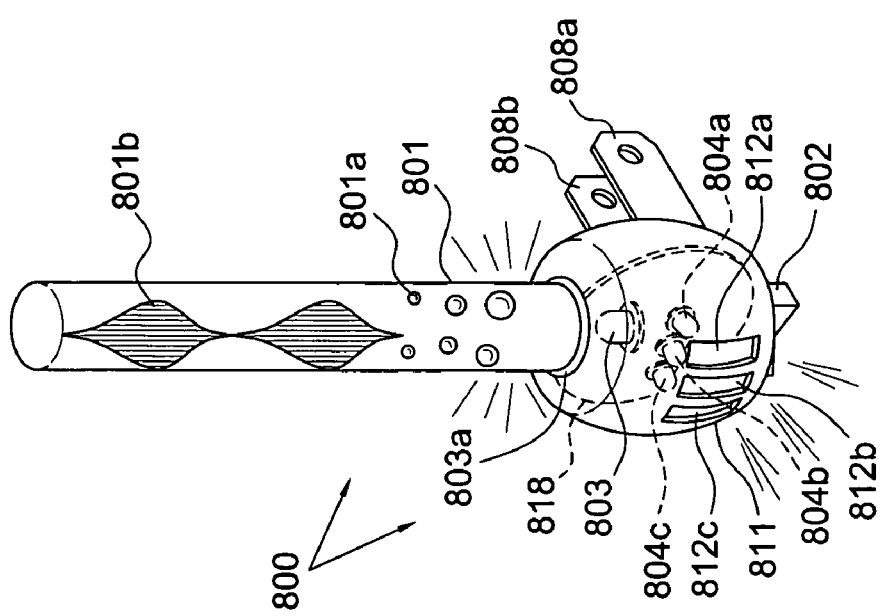
FIG. 4 is a perspective view of a preferred embodiment which has a decorative unit on top of the housing with at least two light source sets to provide desired light effects to the top decorative unit and openings, windows, holes, and/or cut-outs.

FIG. 4 shows a two light source night light (800) having a solid plastic injection pole on the top of the housing (811). The solid plastic injection pole may include cosmetic designs within such as Air Bubbles (801a), laser carving (801b), and geometric shapes with thickness so as to create optics effects. The housing can be any design to match market requirements such as a vase (102) shape to match the fiber optics flower (200), a bomb shape housing (910) to fit the lava top (911), or a half egg shape housing (81) to fit the top half egg shape (82). The housing houses the circuit, light source set(s), prong means, switch means, and control means with proper sealing to prevent kids or people to touch the live wires.

As shown in FIG. 4, the top plastic piece (801) is made by plastic injection, blow-molding, or other process to have a decorative and eye-catching appearance such as that of a solid plastic unit with air arranged inside (801a), a laser carved linear inside (801b), or a plastic container with liquid medium, miniatures, reflective materials, or floating materials within, poly designs, or dry flowers to form special decorative designs.

The housing includes a first light source set (803) to supply light beams to the one opening (803a) and a second light source set (804) including LEDs (804a) (804b) (804c) totaling three LED(s) positioned relative to windows or areas (812a) (812b) (812c) to enable the light beams to be emitted out to viewers. The construction of the windows, openings, cut-outs, holes, or other areas depends on the housing material, which may be transparent, translucent, non-transparent, and/or opaque, so that one can use the proper selection from the group consisting of windows, openings, cut-outs, holes, or areas on the preferred night light to obtain desired effects. For example, the windows (812a) (812b) (812c) can be areas of the housing through which light passes to avoid the need for openings or cut-outs.

The desired light emitting angle can be adjustable by bending the LED(s) legs to get a proper light beam direction. The prong means (808a) (808b) are securely installed within the housing (811) and connected with the circuit (818) to supply electric signals to the multiple light source sets.

FIG. 5 shows a two light source night light (900) having a top decorative unit made up of a plastic or glass container (911) filled with a liquid medium. A variety of stuff may be included within the liquid medium, such as miniature poly stuff (901d), miniature floating stuff (81a) (81b) (81c), miniature shells (not shown), dried flowers (not shown), sea shells (not shown), reflective material (901a) (901b) (901c) (81d), different density liquids, or the like which are available from the market place. The housing (910) has multiple openings (904d), windows (904a), cut-outs (904b), holes (904c), and/or areas through which light passes through the housing, to allow the second light source sets (904a) (904b) to pass light beams through the openings (904d), windows (904a), cut-outs (904b), and holes (904c) of the said housing (910). The housing (910) has a top opening (910a) to install the decorative unit (911) with the first light source sets (903) at a proper alignment to allow the light beams pass though the liquid medium and miniatures (901d), reflective material (901b), other reflective material (901c), and poly miniatures (901d) to provide a good decorative unit (911). The housing (910) may incorporate at least one heat element (909a) (909b) which will emit heat to cause the heat-sensitive liquid to have fluid movement and cause all the inner reflective materials (901b) (901c) (901a) to move and reflect incoming light beams to a viewers' eyes for very attractive light effects. A manual switch or automatic photo sensor device (902) may be incorporated with the driver circuit to make the light more practical for human life.

FIG. 6 illustrates another embodiment with a solid plastic cone (41) as a decorative unit on top of housing (42). The plastic cone (41) has an air bubble within so as to cause the light beams to be reflected and deflected to a viewers' eye to provide good optics effects. The housing has two light source sets (44) (45) to supply the top opening (44a) and front window (45a) with good light beams to be emitted out from decorative unit cone (41) and the front area of the housing. A manual or automatic sensor switch (48) may be installed on the housing to let people control the night light.

FIG. 7 illustrates another embodiment with a liquid container on top as a decorative unit (82) of the housing (81). The liquid container has at least one miniature fish (81a) (81b) (81c), and at least one reflective material (81d) to provide the container with a very eye-catching decorative unit for the night light. The two light source sets (83a) and (83b) constitute a first light source set to offer the light effects to the said container. The light source set (84) provides the light effects to the window (84a) to provide an otherwise dark front area such as the floor with good light illumination.

The openings (803a) (910a) (44a) (83) for the top decorative unit of the housing (811) (910) (42) (81) can receive the top decorative unit within. The windows (812a)(812b) (812c) (904a) (904b) (904c) (904d) (45a) (84a) may take the form of openings, windows, cut-outs, stencils, holes, or light-transmitting areas depending on whether the housing material is transparent, translucent, opaque, or non-transparent, as long as the windows allow light beams to pass through. The housing may made of plastic, metal, ceramic, pottery, or other chemical compound to meet the UL standard.

FIGS. 8 and 9 show decorative units (50) (60) installed on top of the housing (51)(61) and arranged to get illumination from a single light source set (51) (61) for decoration, heat and illumination. The preferred light source set in this embodiment is a bulb with specification from 4 Watt to 7 Watt. The multiple openings, windows (53), holes (63), cut-outs or areas depend on the market requirement and UL standard. These may have stencils, front sheets, lenses, filters, and/or mesh so as to meet all requirements and turn the openings into windows. The single light source set (51) (61) illuminates the top decorative unit (50) (60) and also the openings, windows, cut-outs (53) (63) of the housing. The openings, windows, cut-outs, and/or areas (53) (63) are lower than the light source set's filament position which will not affect the hot air flow to upper decorative units (50) (60). The openings, windows, cut-outs, and/or areas (53)(63) lower than the filament illuminate the floor to make the night light more practical for consumers. This is an alternative advantage feature of the current invention, i.e., the provision of a single light source set with a plurality of the lighted areas on the night light rather than the multiple light source sets of the above-described embodiments. The top decorative unit in the form of the liquid medium container (50) (60) can have floating stuff (52b) (62b) in the form, for example, of a fish and duck, reflective material (52a) (62a) in the form, for example, of a star and heart, and poly characters (52*c*) (62*c*) in the form, for example, of a fish and tree which are on the bottom of the decorative unit.

FIG. 10 shows an LED bubble light which has multiple light source sets (71) to supply light beams to a top decorative unit (73) which in the form of a solid plastic pole with interior air bubbles created during an injection molding process. The other light source sets (72*a*) (72*b*) located inside the light transmitting housing so that the light will be seen from viewers through areas (78*a*) (78*b*) with brighter spots and wider light rings from outside. an appropriate circuit (not shown), prong means (77) and sensor means (76) are also sealed inside the housing to comply with the safety standard requirement. In this embodiment, there are only light transmitting areas of the housing although windows, openings, cut-outs, or holes may of course be substituted depending on housing material.

FIG. 11 shows a preferred fragrance element with dimensions of 61.8×33.8×27.5 mm for length×width×height, plus or minus 50%. The night light with smell device has a compartment similar to that shown in FIG. 2 (600) or FIG. 3 (610) with appropriate dimensions to allow the fragrance element(s) to fit into the space. In addition, to make the smell spread out more quickly to a wider area, one may incorporate heat element(s), fan(s), motor(s), gear set(s), resistor film(s), resistor unit(s), switch device(s). The night light has at least 2 light source sets to provide an excellent value with an attractive appearance. For example, FIG. 12 shows a night light (98) having fiber optic flowers (not shown) on top as a decorative unit with a vase shape housing (90) having multiple of windows or openings (95*a*) (95*b*)(95*c*) (95*d*) near the vase lower base. The first LED(s) light source set (93) supplies light to the fiber optics for splendid light effects and the second LED(s) light source sets (94*a*) (94*b*) supply the vase's windows or openings with brighter light to provide floor illumination. The vase housing (90) has a fragrance compartment (91) on its back side to allow the fragrance element (99) to fit into the installation.

Although the invention has been described with respect to preferred embodiments, it will be appreciated that any alternative or equivalent elements or designs still fall within the scope of the invention, which is not limited by the above discussion and afore-mentioned details. The alternative or equivalent arrangement, process, installation or the like design, changes from the current invention still fall within the scope of the current invention.

The invention claimed is:

1. A multiple light source night light with a fiber optics unit, including:
   first and second light source sets within the night light, each of the light source providing a different light performance,
   wherein the first and second light source sets are selected from the group consisting of at least one LED, EL, OLED, neon bulb, gas filled bulb, incandescent bulb, fluorescent tube, halogen bulb and conventional light means, and
   wherein said first and second light source sets are sealed within a housing to enable a viewer to see the respective light performances of the light source sets,
   the improvement wherein:
   the first light source set supplies light beams to the fiber optics unit for providing light effects and the light functions upon being driven by a circuit included in the night light, and
   the second light source set supplies light beams that pass in a desired direction through light passages selected from the group consisting of windows, cut-outs, openings, light-transmitting areas of the housing, and holes.

2. A multiple light source night light with a smell device, including:
   at least two light source sets installed within a housing and connected with a circuit and prong means to get a desired electric signal to cause the first and second light source sets to exhibit pre-determined light effects while the prong means are connected with a power source,
   wherein said night light is further incorporated with the smell device and a heat element to make a fragrance material spread out to wider areas while the prong means are connected with a power source, and
   further comprising control means incorporated with the circuit for providing functions selected from the group consisting of operating a switch, sensor, fan, mechanical device, chemical compound, fragrance dispenser in any form, deodorizer device, $O_3$ generator, and heater film with adjustable kits to provide multiple functions of said night light with smell device.

3. A multiple light source night light, including:
   at least two light source sets installed within a housing,
   wherein said two of light source sets include first and second light sets, both of which LEDs,
   the improvement wherein:
   the first and second light source sets only emit single color light beams to viewers while the prong means connect to a power source,
   the night light is arranged to incorporate a switch means and heater means,
   and further comprising decorative means incorporated with the said housing to make said night light have a valuable appearance and selected from the group consisting of any combination of fiber optics, a solid plastic injection with air inside, a liquid medium unit with miniature stuff inside, a liquid medium unit with reflective stuff inside, a liquid medium unit with desired stuff inside, a textured lens, and a stain-glass device.

4. A multiple light source night light with a top decorative unit, including:
   at least two light source sets including first and second light sources to light beams to different locations selected from the ground consisting of openings, windows, holes, cut-outs, and light-transmitting areas of a housing.
   wherein the first light source set supplies the light beams to a decorative unit selected from the group consisting of a fiber optics device, liquid medium device, solid plastic device, and plastic injection device with decorative designs to provide expected light effects, and
   wherein the second light source set supplies light beams to the viewer through said openings, windows, holes, cut-outs, and light-emitting areas.

5. A night light having multiple lighted areas, including:
   at least one light source set installed within a housing,
   wherein said housing includes at least two areas having separate and discrete light passages selected from the group consisting of windows, openings, cut-outs, holes, light-transmitting areas of the housing, ends of the housing, and sides of the housing to allow light beams to be emitted out to viewers directly or indirectly,
   the improvement wherein:
   each of said windows, openings, cut-outs, holes, areas, ends, and sides of the housing incorporates different decorated units selected from the group consisting of a lamp shade, lens, plastic injection pieces, filter, stencil, glass device, decoration stuff, toy, blow-mold items, stained glass with frame, ceramic item, liquid medium device with miniature stuff inside, and solid plastic piece with laser carving inside, and fiber optics device which allows the light to pass through to viewers.

6. A multiple light source night light with smell device, including:
- at least two light source sets to provide the night light with desired light effects and functions:
- at least one compartment installed with fragrance elements, said compartment having the approximate dimensions 61.8 mm (length)×33.8 mm (width)×7.6 mm (heights) plus or minus 50%, the improvement wherein:
- the night light includes a heat element selected from the group consisting of an electric component, resistor film, and resistor units to connect with electricity to generate heat at pre-determined temperatures to cause the fragrance elements to spread fragrance to a wider area, and
- an optional additional device selected from the group consisting of a fan device, motor device, and gear device.

* * * * *